United States Patent [19]

Shaw

[11] 3,957,606

[45] May 18, 1976

[54] ELECTROCHEMICAL PRODUCTION OF SUBSTITUTED PYRIDINES

[75] Inventor: Robert Alfred Shaw, Chislehurst, England

[73] Assignee: Birkbeck College, England

[22] Filed: Oct. 18, 1974

[21] Appl. No.: 516,196

[30] Foreign Application Priority Data
Oct. 25, 1973 United Kingdom............... 49756/73

[52] U.S. Cl. ............................. 204/165; 260/290 P
[51] Int. Cl.² ..................... B01K 1/00; C07C 213/02
[58] Field of Search........................... 204/165, 177

[56] References Cited
UNITED STATES PATENTS

| | | | |
|---|---|---|---|
| 3,275,540 | 9/1966 | McBride | 204/165 |
| 3,281,346 | 10/1966 | Brown et al. | 204/165 |
| 3,397,132 | 8/1968 | Wolinski | 204/165 |
| 3,475,307 | 10/1969 | Knox et al. | 204/168 |
| 3,629,083 | 12/1971 | Brendle | 204/165 |

FOREIGN PATENTS OR APPLICATIONS 2,038,272  3/1972  Germany ........................ 204/165

*Primary Examiner*—F. C. Edmundson
*Attorney, Agent, or Firm*—Wenderoth, Lind & Ponack

[57] ABSTRACT

A process for preparing pyridine derivatives, particularly dipyridyls which are intermediates for the production of herbicides and photographic and metal treatment chemicals, comprises passing an electrical discharge, preferably a silent electrical discharge of the type used in ozoniser equipment, through pyridine or pyridine derivatives in the liquid or vapour state in the absence of oxygen or oxygen-containing compounds.

6 Claims, 1 Drawing Figure

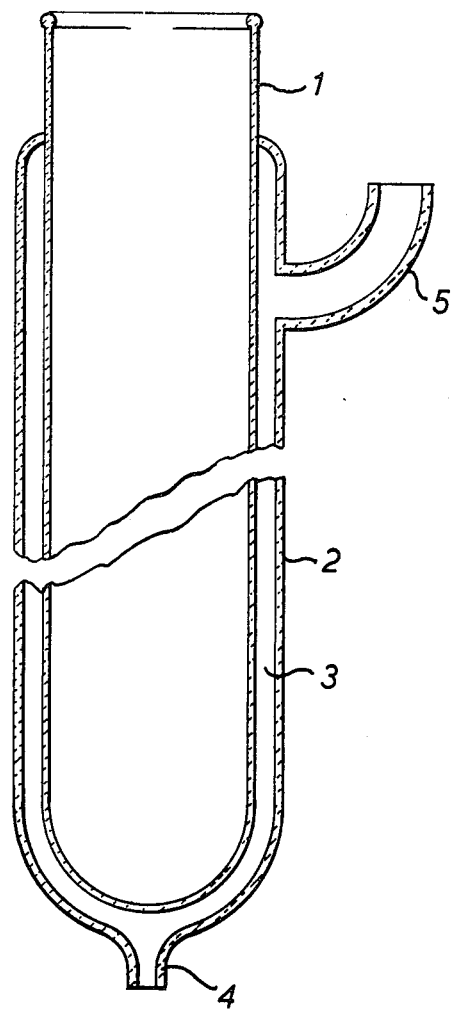

3,957,606

ELECTROCHEMICAL PRODUCTION OF SUBSTITUTED PYRIDINES

BACKGROUND OF THE INVENTION

This invention relates to the production of substituted pyridines and has particular application to the production of dipyridyls and derivatives thereof. Dipyridyls are important intermediates in the production of herbicides and of photographic and metal treatment chemicals.

Hitherto conventional processes for the preparation of dipyridyls have usually involved the preparation, as an intermediate, of a metal derivative of pyridine, frequently a sodium derivative. However, the production of dipyridyls by such processes tends to be hazardous and is also corrosive and comparatively expensive.

SUMMARY OF THE INVENTION

It has now been discovered that substituted pyridines of the general formula $C_5H_{5-n}NR_n$ where R represents a group or groups selected from alkyl, amino, cyano, carboxyl, pyridyl and pyridyl substituted by one or more of the groups alkyl, amino, cyano and carboxyl, and n is an integer of from 1 to 5, may conveniently be prepared by a process which comprises passing an electrical discharge through pyridine or one or more alkyl-substituted pyridines or a mixture of pyridine with one or more alkyl-substituted pyridines, in the liquid or vapour state and in the substantial absence of oxygen, water and other reactive oxygen-containing compounds. The process has been found to be particularly useful for the production of dipyridyls, i.e. substituted pyridines of the above general formula in which R represents an unsubstituted pyridyl radical and $n$ represents one, and in particular for producing 2:2' dipyridyl and 4:4' dipyridyl.

As will be seen, the process of this invention avoids the use of the hazardous metal derivatives of pyridine and the corrosive reaction conditions attendant thereon, and is also relatively inexpensive to operate. Although, as is described hereafter, the order of electrical voltage which it is preferred to use to provide the electrical discharge in the process is relatively high, the electrical current involved is low and thus the electrical energy requirements are modest.

The process may be operated at ambient or elevated temperature, for example at 20°–100°C or higher, at pressures lower than atmospheric, at atmospheric pressure or higher than atmospheric pressure.

Suitable diluents include hydrogen, nitrogen, the inert gases, ammonia, hydrogen cyanide and gaseous or volatile hydrocarbons, according to the products which are required.

The electrical discharge may be alternating or direct and may pass directly through the substrate between electrodes comprising wires, rods or sheets of metal; mercury or carbon may also be used as electrode materials. Alternatively, and preferably, there may be employed what is known as the silent electrical discharge, wherein the discharge space is bounded by dielectric materials. This is characteristically used in the manufacture of ozone, and it has been found that by its use, yields of dipyridyls of the order of 50%, based upon pyridine conversion, may be obtained. Suitable voltages are of the order of at least 1000 volts, and when using the silent electrical discharge, a voltage of between 2.5 and 10.0 kilovolts, for example about 5 kilovolts at from 10 to 100 cycles or more, and usually about 50 cycles per second has been found particularly suitable for obtaining good conversion of pyridine to dipyridyls.

The process of the invention appears (though we do not limit ourselves to this theory) not to proceed via thermal dissociation but through the electrically induced formation of active species, which may be ions, free radicals or excited molecules and may comprise active forms of pyridine itself or products of ring-breaking such as cyano, imino, or hydrocarbon fragments, which can then combine in various ways controlled by activity, concentration and mobility factors. Thus it has been found that, when a discharge directly through the substrate is used, the major products are hydrogen cyanide and the various isomeric cyano- and methyl-pyridines; whereas when the silent electrical discharge is used, with interpolation of a dielectric between the electrodes and the substrate, the major products are dipyridyls, together with minor amounts of hydrogen cyanide and alkyl-, amino-, and cyano-pyridines.

From the point of view of dipyridyl production, the latter products represent a waste of raw material and it has been found that, using the silent electrical discharge, their formation can readily be minimised by control of the operating parameters applied voltage, pressure, reaction time and temperature. Thus, using the technique and apparatus described in the examples hereafter, an applied voltage in the range from 2.5 to 10 kilovolts, preferably about 5 kilovolts, at a frequency of 10 to 100 cycles per second, preferably about 50 cycles per second, a pressure of 15 to 45 mm. (partly arising from the vapour pressure of pyridine and partly from the vapour pressure of the volatile reaction products), a reaction time of the order of 10 hours, and a temperature of 80°±5°C, were found to give optimum conversion of pyridine to dipyridyls. Longer reaction times and higher pressures, temperatures and/or voltages caused, inter alia, the formation of increasing amounts of a non-volatile tar whose analysis suggests that it may be a mixture of polypyridyls, poly(vinylpyridines) and oxygen-containing products arising from air leakage into the equipment.

Although in the examples hereafter the products of the process of this invention have, for analytical purposes, been isolated and identified by gas/liquid chromatography, it will be appreciated that any conventional separation technique or combination of conventional separation techniques, based on differences in the physical and/or chemical properties of the compounds in the mixture resulting from the electrochemical reaction, such as solvent extraction and distillation, may be employed to isolate individual desired pyridine derivatives or desired mixtures of specific pyridine derivatives. For example the reaction mixture may firstly be distilled at atmospheric pressure to remove pyridine, alkyl substituted pyridines and other relatively volatile constituents of the reaction mixture. If the reaction mixture is then boiled with dilute hydrochloric acid the cyano pyridines are converted to the corresponding carboxylic acids which due to their low solubility precipitate on cooling and can be filtered off. It should be pointed out that the carboxyl derivatives may also be prepared by conventional oxidation of the corresponding methyl derivatives. The amino pyridine derivatives remain in solution as their HCl acid addition salts.

The dipyridyls may be separated from one another by conventional techniques, for example by fractional distillation, after basifying the mixture to be distilled, if appropriate, or by the method described in U.K. Patent specification No. 996,569 for isolating 4:4' dipyridyls. In the latter method the mixture of dipyridyls is cooled to below 60°C in the presence of water so that the relatively insoluble hydrate of 4:4' dipyridyl is precipitated. The crystals of the hydrate are removed and 4:4' dipyridyl is regenerated from the hydrate heating the crystals above 60°C.

Although the conditions used in the examples hereafter, whereby in effect pyridine was refluxed in vacuo in the dishcharge chamber, gave substantial yields of dipyridyls, the process of the invention is adaptable to continuous operation, with comparatively short residence time, separation of products and recycling of unreacted pyridine, the more so since under the conditions of the examples, employing a reaction period as long as ten hours or more, substantial amounts of pyridine still remained unreacted. Such continuous operation, e.g. at sub-atmospheric, atmospheric or super-atmospheric pressure and with or without the addition of an inert diluent, for example a rare gas, might also be expected to minimise the formation of unwanted by-products where the desired products are dipyridyls. On the other hand, if amino-, alkyl-, or cyano-pyridines are required (e.g. in the latter two cases for subsequent conversion to pyridine carboxylic acids), it could be expected to be advantageous to incorporate in the reaction stream respectively ammonia, hydrocarbons or hydrogen cyanide. As will be readily appreciated dipyridyls produced by the process of this invention may readily be converted to acid addition salts and may also be converted by conventional techniques to herbicidal quaternary salts, for example by reaction with alkylating agents such as methyl chloride, methyl sulphate and ethylene dibromide.

BRIEF DESCRIPTION OF THE DRAWING

In the examples hereafter a reactor of the conventional "ozoniser" type was employed which is shown in section in the accompanying drawing.

The cell of the reactor was made of "Pyrex" (Registered Trade Mark) heat resistant glass and consisted of an inner round-bottomed cylindrical wall 1 surrounded by a coaxial cylindrical jacket 2 so as to form a reaction space 3 of annular cross-section. An inlet 4 connected to a reservoir (not shown) was provided at the base of the cell and an outlet 5 was provided in the upper part of the jacket. The height of the cell was 30 cm., the overall diameter 5.5 cm. and width of the annular reaction space 0.75 cm. The cell had an effective reaction surface area of 370 cm.$^2$ when used in the Examples hereafter. The cell was connected via side outlet 5 through a magnetic valve (not shown) to a pumping system (not shown). the magnetic valve being opened or closed through a relay connected to a manostat (not shown) comprising a U-tube containing mercury making or breaking contact, according to the pressure within the reaction system, with an iron wire (not shown) set at a predetermined height to achieve control of pressure at the desired level by connecting the cell to the pumping system for the requisite time. The reservoir, connected to outlet 5 of the cell, was maintained at a selected temperature, ± 5°C, in a constant temperature bath and the upper part of the cell was cooled in a mixture of acetone and solid carbon dioxide. Connection was provided to the high-voltage output side of a transformer (0–35 kilovolts) via a copper wire electrode at the axis of the cell, and the exterior surface of the cell was coated with aluminium foil connected to earth. Although, as mentioned above, a reactor of the conventional "ozoniser" type was employed in the Examples having an annular-section reaction space, it will be apparent that reactors of other patterns (e.g. employing parallel plates of dielectric) can also be used, as also can dielectrics other than glass, e.g. ceramics, silica or suitably resistant polymers. The reaction space can also contain filler materials such as glass beads.

Following are specific examples of the process of this invention.

DESCRIPTION OF PREFERRED EMBODIMENTS

EXAMPLE 1

Pure pyridine (15 g.) was transferred by vacuum evaporation to the reservoir connected to inlet 4 of the cell hereinbefore described. The pressure of the system was set at 20 mm. and the constant temperature bath for the reservoir was set at 80°C±5°C. These conditions were maintained for ten hours whilst a voltage of 5 kilovolts at 50 cycles per second was applied. The reaction product was extracted with diethyl ether, in which the tar formed during the reaction was insoluble, and the volatile products were identified by gas/liquid chromatography, using nitrogen as the carrier gas and Carbowax 20M (Carbowax is a Registered Trade Mark) as the stationary phase. A yield of 43.5% by weight of dipyridyls, based upon pyridine converted and comprising roughly equal amounts of the 2,2' and 4,4' isomers, together with a much smaller amount (roughly one-tenth of the total) of a third unidentified isomer, was obtained; together with minor amounts of all the possible isomeric mono-substituted amino-, cyano- and methyl-pyridines and some ethyl- and dimethyl-pyridines. Individual peaks on the chromatogram were identified by reference to authentic samples. 2.1 g. of tar was formed and 6.0 g. of unreacted pyridine recovered.

EXAMPLE 2

With conditions otherwise as in Example 1, the reaction pressure was maintained at 25 mm. The yield of dipyridyls, of similar isomeric composition to that of Example 1, was found to be 33.9%, the amount of tar 3.5 g. and of recovered pyridine 5.25 g.

EXAMPLE 3

Using the same equipment as used in Example 1, an operating pressure of 35 mm., a reservoir temperature of 90 ± 5°C, an applied voltage of 15.5 kilovolts and a reaction time of 5.5 hours were employed. From the standard charge of 15 g. of pyridine, a yield of 27.5% of dipyridyls, of similar isomeric composition to that of Example 1 was obtained, together with 2.0 g. of tar and 8.5 g. of recovered pyridine. If the reaction time was increased to 16.5 hours, conditions otherwise being as in this example, the yield of dipyridyls had fallen to 10.7%, the tar content had risen to 9.5 g. and the recovered pyridine had fallen to 1.8 g.

EXAMPLE 4

Using the same equipment as that used in Example 1, a pressure of 30 mm., a reservoir temperature of 90±

5°C, a voltage of 2.5 kilovolts and a reaction time of 10 hours were employed in this example. From the standard charge of 15 g. of pyridine, a yield of 15.6% of dipyridyls, of similar isomeric composition to that of Example 1, was obtained, together with 0.8 g. of tar and 11.1 g. of recovered pyridine. If the applied voltage was increased to 15.5 kilovolts, conditions otherwise being as in this example, the yield of dipyridyls rose to 22.0%, the tar content to 5.75 g., and the recovered pyridine had fallen to 1.5 g.

I claim:

1. A process for preparing substituted pyridines of the general formula $C_5H_{5-n}NR_n$, and acid addition salts thereof, where R represents at least one member selected from the group consisting of alkyl, amino, cyano, carboxyl, pyridyl and pyridyl substituted by at least one member selected from the group consisting of alkyl, amino, cyano and carboxyl, and $n$ represents an integer of from 1 to 5 which process comprises passing a silent electrical discharge through pyridine, or at least one alkyl-substituted pyridine, or mixtures of pyridine with at least one alkyl-substituted pyridine wherein the voltage of said alternating electrical current is in the range from 2.5 to 10Kv and the frequency of said alternating current is in the range from 10 to 100 cycles per second.

2. A process as claimed in claim 1 wherein the reaction medium contains as an inert diluent one of the rare gases, or a mixture of rare gases.

3. A process as claimed in claim 1 wherein R represents pyridyl and $n$ represents 1.

4. A process for preparing substituted pyridines as claimed in claim 1 wherein R represents pyridyl and $n$ represents 1 which process comprises passing an alternating electrical current through a space containing pyridine in the vapor or liquid state, the said space being bounded by dielectric materials.

5. A process as claimed in claim 1 wherein the dipyridyls are subsequently recovered by fractional distillation.

6. A process for preparing 2:2' and 4:4' dipyridyls which process comprises
   passing an alternating electrical current at a potential difference of from 2.5 to 10.0 Kv and at a frequency of from 10 to 100 cycles per second through a space bounded by dielectric materials and containing pyridine in the liquid or vapor state in the absence of reactive materials containing oxygen and thereafter separating the
   2:2' and 4:4' dipyridyls from the resulting reaction mixture.

* * * * *